US011020011B2

(12) United States Patent
An et al.

(10) Patent No.: US 11,020,011 B2
(45) Date of Patent: Jun. 1, 2021

(54) ESTIMATE DIASTOLIC PRESSURE (71) Applicant: Cardiac Pacemakers, Inc., St. Paul, MN (US)

(72) Inventors: Qi An, Blaine, MN (US); Pramodsingh Hirasingh Thakur, Woodbury, MN (US); Michael J. Kane, Roseville, MN (US); Yinghong Yu, Shoreview, MN (US); Jeffrey E. Stahmann, Ramsey, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 538 days.

(21) Appl. No.: 15/654,776

(22) Filed: Jul. 20, 2017

(65) Prior Publication Data

US 2018/0020930 A1    Jan. 25, 2018

Related U.S. Application Data (60) Provisional application No. 62/364,746, filed on Jul. 20, 2016.

(51) Int. Cl.
| | |
|---|---|
| *A61B 5/02* | (2006.01) |
| *A61B 5/0215* | (2006.01) |
| *A61N 1/365* | (2006.01) |
| *A61N 1/372* | (2006.01) |
| *A61B 7/04* | (2006.01) |

(52) U.S. Cl.
CPC ........ *A61B 5/0215* (2013.01); *A61B 5/02028* (2013.01); *A61B 5/02158* (2013.01); *A61N 1/36521* (2013.01); *A61N 1/36564* (2013.01); *A61N 1/36578* (2013.01); *A61N 1/37247* (2013.01); *A61N 1/37282* (2013.01); *A61N 1/37288* (2013.01); *A61B 7/04* (2013.01)

(58) Field of Classification Search
CPC .............. A61B 5/0215; A61B 5/02158; A61B 5/02028; A61B 7/04; A61N 1/37282; A61N 1/36578; A61N 1/37247; A61N 1/37288; A61N 1/36564; A61N 1/36521
See application file for complete search history.

(56) References Cited

U.S. PATENT DOCUMENTS

| | | | | |
|---|---|---|---|---|
| 4,203,451 | A * | 5/1980 | Panico | A61B 5/022 600/485 |
| 2003/0153837 | A1 * | 8/2003 | McIntyre | A61B 5/021 600/485 |
| 2008/0091115 | A1 * | 4/2008 | Popov | A61B 5/021 600/528 |
| 2009/0275843 | A1 * | 11/2009 | Karamanoglu | A61B 5/02028 600/486 |
| 2012/0157856 | A1 * | 6/2012 | An | A61B 5/0816 600/484 |
| 2014/0107505 | A1 * | 4/2014 | Marmor | A61B 5/02007 600/486 |

(Continued)

*Primary Examiner* — Navin Natnithithadha
*Assistant Examiner* — Andrey Shostak
(74) *Attorney, Agent, or Firm* — Schwegman Lundberg & Woessner, P.A.

(57) ABSTRACT

Arterial diastolic pressure of a patient can be estimated using ventricular pressure information of a heart of the patient and heart sound information of the heart of the patient, such as a timing of at least one of a first heart sound (S1) or a second heat sound (S2), in certain examples, adjusted by a respective correction factor.

11 Claims, 4 Drawing Sheets

(56) References Cited

U.S. PATENT DOCUMENTS

| | | |
|---|---|---|
| 2015/0174413 A1 | 6/2015 | Stahmann et al. |
| 2015/0224320 A1 | 8/2015 | Stahmann |
| 2015/0324962 A1* | 11/2015 | Itu .............................. G06T 7/00 382/130 |
| 2016/0067490 A1* | 3/2016 | Carney .................. A61N 1/368 607/17 |

* cited by examiner

ESTIMATE DIASTOLIC PRESSURE

CLAIM OF PRIORITY

This application claims the benefit of priority under 35 U.S.C. § 119(e) of U.S. Provisional Patent Application Ser. No. 62/364,746, filed on Jul. 20, 2016, which is herein incorporated by reference in its entirety.

TECHNICAL FIELD

This document relates generally to medical devices, and more particularly, but not by way of limitation, to systems, devices, and methods to estimate diastolic pressure.

BACKGROUND

Implantable medical devices, such as cardiac rhythm management (CRM) devices, can be used to monitor, detect, or treat various cardiac conditions that can result in a reduced ability of a heart to sufficiently deliver blood to a body. In some cases, heart conditions may lead to rapid, irregular, or inefficient heart contractions, etc. To alleviate one or more of these conditions, various medical devices can be implanted in a patient's body to monitor heart activity or to provide electrical stimulation to optimize or control contractions of the heart.

Traditional cardiac rhythm management (CRM) devices, such as pacemakers or defibrillators, include subcutaneous devices implanted in a chest of a patient, having one or more leads to position one or more electrodes or other sensors at various locations in the heart, such as in one or more of the atria or ventricles. In certain examples, the one or more leads can include a pressure sensor positioned in the heart and coupled to the CRM device through a conductor in the lead. Separate from, or in addition to, the one or more electrodes or other sensors of the leads, the CRM device can include one or more electrodes or other sensors (e.g., a pressure sensor, an accelerometer, a gyroscope, a microphone, etc.) powered by a power source in the CRM device. The one or more electrodes or other sensors of the leads, the CRM device, or a combination thereof, can be configured detect physiologic information from, or provide one or more therapies or stimulation to, the patient.

For example, the CRM device or the one or more leads can include an acoustic sensor, such as an accelerometer, a microphone, or one or more other acoustic sensors configured to detect body sounds from a patient, such as cardiac murmurs, respiratory sounds, heart sounds, mitral regurgitation, mitral stenosis, or other body sounds. The body sounds, or other physiologic information, can be used to diagnose one or more physiologic conditions, provide an alert, or to control one or more therapies.

However, implantable CRM devices typically require an incision in the chest to implant the device in a pocket under the skin, which, in certain examples, can become infected, reduce mobility near the implant site, migrate, or leave a scar or lump where the device is implanted. Further, leads positioned in the heart may cause complications, becoming dislodged, breaking, migrating, or even perforating the heart.

Leadless cardiac pacemakers (LCP) have been developed that can detect physiologic information from or provide one or more therapies or stimulation to the heart without traditional lead or implantable CRM device complications. Such LCP devices are typically small, self-contained devices (e.g., smaller than traditional implantable CRM devices), and in certain examples, have more limited power and processing capabilities than a traditional CRM device.

In certain examples, multiple LCP devices can be implanted in the heart to detect physiologic information from, or provide one or more therapies or stimulation to, one or more chambers of the heart. The multiple LCP devices can communicate between themselves, or one or more other implanted or external devices.

SUMMARY

This document discusses, among other things, systems and methods to estimate an arterial diastolic pressure of a patient using ventricular pressure information and heart sound information of the heart of the patient. The systems and methods disclosed herein can estimate a systemic diastolic pressure of the patient using a left ventricular pressure of the patient and a timing of at least one of a first heart sound (S1) or a second heat sound (S2), or a pulmonary diastolic pressure of the patient using a right ventricular pressure of the patient and a timing of at least one of the S1 or the S2. In certain examples, the timing of one or more of the S1 or the S2 can be adjusted by a correction factor.

This summary is intended to provide an overview of subject matter of the present patent application. It is not intended to provide an exclusive or exhaustive explanation of the disclosure. The detailed description is included to provide further information about the present patent application. Other aspects of the disclosure will be apparent to persons skilled in the art upon reading and understanding the following detailed description and viewing the drawings that form a part thereof, each of which are not to be taken in a limiting sense.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Clinically, blood pressure is a measurement of pressure exerted by circulating blood upon the walls of blood vessels, typically the arteries, such as the aorta, as the blood leaves the heart for the rest of the body. Blood pressure is generally expressed in terms of the maximum pressure, "systolic", over the minimum pressure, "diastolic", measured in millimeters of mercury (mm Hg).

The present inventors have recognized, among other things, that systemic arterial diastolic pressure can be determined using a pressure of the left ventricle in combination with another physiologic signal, such as heart sounds, that can identify the closing of the aortic valve, which isolates the left ventricle from the aorta as the left ventricle relaxes following a contraction and the pressure in the left ventricle falls below the pressure in the aorta, or, separately or in combination therewith, that can identify the opening of the aortic valve as the left ventricle contracts and the pressure in the left ventricle exceeds the pressure in the aorta. Determination of such systemic arterial diastolic pressure, as described herein, can be used to improve operation or programming of a medical device including, coupled to, or configured to receive pressure information from a pressure sensor.

In certain examples, a pressure sensor can be placed in the left ventricle to directly sense the left ventricular pressure of the heart, such as by using a pressure sensor in a leadless cardiac pacemaker (LCP) positioned in the left ventricle. In other examples, the pressure of the left ventricle can be estimated, for example, using a pressure of another chamber of the heart (e.g., a right ventricle, etc.), or using a lead positioned proximate to the left ventricle, such as through the coronary sinus into a posterior or lateral cardiac vein proximate the left ventricle, etc.

Filling of the left ventricular from the left atrium begins as the left ventricle relaxes following a contraction, and the pressure in the left ventricle falls below the pressure of the left atrium, opening the mitral valve.

As the left ventricle contracts, the pressure in the left ventricle quickly rises. When the pressure in the left ventricle rises above the pressure of the left atrium, the mitral valve snaps shut, isolating the left ventricle from the left atrium, resulting in a first heart sound (S1). Close in time to the closure of the mitral valve, when the pressure in the left ventricle rises above the pressure of the aorta, the aortic valve opens, allowing blood to exit the left ventricle for the rest of the body through the aorta. The maximum pressure in the left ventricle during contraction, the systolic pressure, is representative of the maximum systemic pressure in the arteries following contraction of the left ventricle (e.g., typically 100-140 mm Hg, etc.).

As the left ventricle relaxes, the pressure in the left ventricle falls quickly. When the pressure in the left ventricle falls below the pressure of the aorta, the aortic valve snaps shut, isolating the left ventricle from the aorta, resulting in a second heart sound (S2). The pressure in the arterial system at the time of the aortic valve opening is the systemic diastolic pressure (e.g., typically 60-100 mm Hg, etc.). Close in time to the closure of the aortic valve, when the pressure in the left ventricle falls below the pressure of the left atrium, the mitral valve opens, allowing filling of the left ventricle. The minimum pressure in the left ventricle following contraction is the left ventricular diastolic pressure (e.g., typically down to 5-10 mm Hg, etc.), different in amplitude, and possibly time, than the systemic diastolic pressure.

The heart valves change state from between open and closed at various times during the cardiac cycle. These valve state changes occur when specific relative pressures are present within the heart and the major vessels leading from the heart (e.g., the aorta). Both the valve states changes and the effects the changes are detectable via various methods. For example valve closure causes vibrations of the walls of the heart that can be detected via an accelerometer or a microphone. The movement of the valves can be detected directly via imaging technologies such as echocardiography and magnetic resonance imaging (MRI) or by intracardiac impedance plethysmography.

Because S2 represents closure of the aortic valve, measurement of a left ventricle pressure signal can be triggered at S2 to estimate the systemic diastolic pressure. In the instance of a split S2, where the aortic and pulmonic valve components (A2 and P2, respectively) of S2 are separate, measurement of the left ventricle pressure signal can be triggered at A2 to estimate the systemic diastolic pressure.

In contrast, S1 represents closure of the mitral valve, which is close in time to the opening of the aortic valve, but not the same. The time period between the onset of electrical systole to the onset of ventricular contraction (e.g., the time period between the Q-wave to S1) can be referred to as the electromechanical activation time (EMAT). Accordingly, to estimate the systemic diastolic pressure, measurement of the left ventricular pressure signal can be triggered at S1, or by S1 in combination with a correction factor, for example, some delay representative of the EMAT.

In certain examples, the correction factor can be dependent on one or more factors, such as one or more of the left ventricular pressure signal (e.g., a derivative of the left ventricular pressure signal (LV dP/dt), etc.), the systemic arterial diastolic pressure, valve function (e.g., one or more of a timing or measurement of one or more heart sound, etc.), heart rate, activity level, posture, paced versus intrinsic contractions, etc. In other examples, both triggered measurements of the left ventricular pressure signal, S1 and S2, can be adjusted using respective correction factors.

In an example, multiple left ventricular pressure measurements can be combined (e.g., averaged or otherwise combined, etc.) to estimate the systemic diastolic pressure. For example, measurement of the left ventricular pressure signal can be triggered at S2, as well as at S1 in combination with a correction factor (or at S1, as well as at S2 in combination with a correction factor) and such measurements can be combined to estimate the systemic diastolic pressure. In an example, one or more of an implantable device (e.g., a LCP, a subcutaneous IMD, etc.) or external device (e.g., an external programmer, etc.) coupled to the pressure sensor and configured to receive heart sound information of the heart can be configured to estimate systemic diastolic pressure in real time, as a weighted average, over various time periods (e.g., 15-minute, daytime, nighttime, daily, weekly, etc.), etc. In certain examples, it can be advantageous to store a representative measurement, or to select certain measurements to store over time. In other examples, it can be advantageous to compute or store the variance of different measurements, etc.

Further, such estimated systemic diastolic pressure can be used, retrospectively or in real-time, to diagnose a physiologic condition, to make a therapy decision, as feedback to adjust a therapy (e.g., vagal stimulation, etc.), or to otherwise judge the efficacy of one or more therapies.

In an example, a pressure sensor of a leadless cardiac pacemaker (LCP) configured for placement in the left ventricle of the heart can be used to sense a left ventricular pressure of the heart. The pressure can be measured during one or more of inactivity, activity, sleep, wakefulness, specific time of day, specific time relating to medication ingestion or injection, or any combination of these times.

The pressure sensor can include a pressure transducer or one or more other pressure sensors configured to be positioned in one or more of an atria or ventricles of a heart, such as a left ventricle (LV), to detect a pressure signal. In an example, the pressure transducer can include a deformable element proximate a rigid element. Each of the deformable and rigid elements can include a conductive surface, such that movement of the deformable surface can be sensed in relation to the rigid element, for example, using a change in capacitance. In other examples, the pressure sensor can include a deformable material, which, when deformed, such as by a change in pressure, can alter a property (e.g., a resistance, an inductance, a capacitance, etc.) of the deformable material. In other examples, one or more other pressure sensors can be used.

Further, as described herein with respect to estimating a systemic diastolic pressure of the patient using left ventricular pressure information and heart sound information of a heart, it is understood that pulmonary diastolic pressure of a patient can be estimated using right ventricular pressure information and heart sound information of a heart, such as using a pressure sensor located in a right ventricle of the heart.

Figure 1:
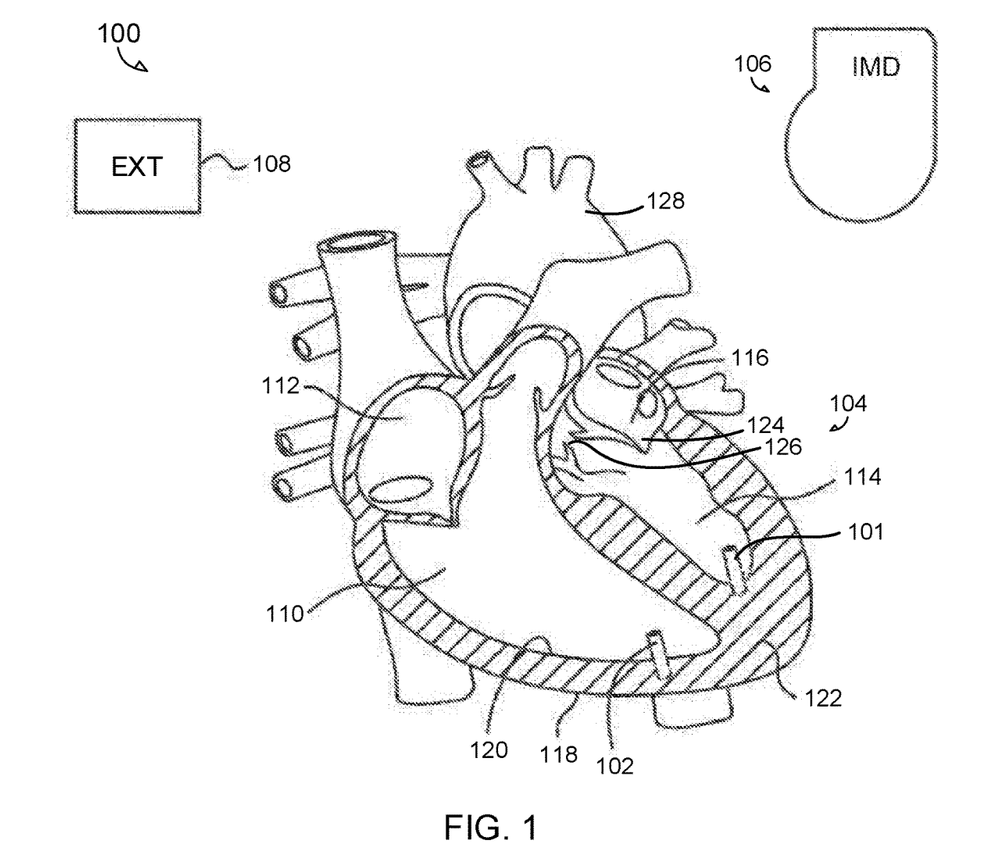
FIG. 1 illustrates generally an example system including first and second leadless cardiac pacemakers (LCP) devices positioned in left and right ventricles of a heart, respectively.

FIG. 1 illustrates generally an example system 100 including first and second leadless cardiac pacemakers (LCP) devices 101, 102 positioned in left and right ventricles 114, 110 of a heart 104, respectively. In an example, the first and second LCP devices 101, 102 can communicate between each other using respective telemetry circuits, to one or more other LCP devices, to an implantable medical device (IMD) 106 (e.g., a subcutaneous cardiac rhythm management (CRM) device, a dedicated communication circuit, etc.), or directly to an external device, such as an external programmer 108, etc.

In other examples, the system 100 can include a single LCP device, or two or more LCP devices for placement in any chamber of the heart, including one or more of a left atrium 116, a right atrium 112, the left ventricle 114, or the right ventricle 110, delivered through the circulatory system of the heart 104 to a location of interest, or implanted through the epicardium 118 or endocardium 120 and into the myocardium 122. Further illustrated in the heart 104 are the aorta 128, the aortic valve 126, and the mitral valve 124.

In an example, the IMD 106 can include a leadless implanted device configured to communicate with one or more of the LCP devices 101, 102, or the IMD 106 can include one or more leads configured to be placed at various locations in the heart, working together with the one or more LCP devices. For example, the IMD 106 can include one or more sensors configured to provide information to one or more of the LCP devices 101, 102. In other examples, one or more of the LCP devices 101, 102 can be configured to supplement sensing in the IMD 106. For example, the IMD 106 can include a CRM device having an accelerometer. In certain examples, one or more of the pressure sensors of the LCP devices 101, 102 can be configured to supplement (e.g., acting as a hydrophone, or a sound pressure sensor) the detected accelerometer signal from the CRM device, such as to enhance detection of one or more physiologic signals, such as heart sounds, or one or more body sounds of the patient.

Figure 2:
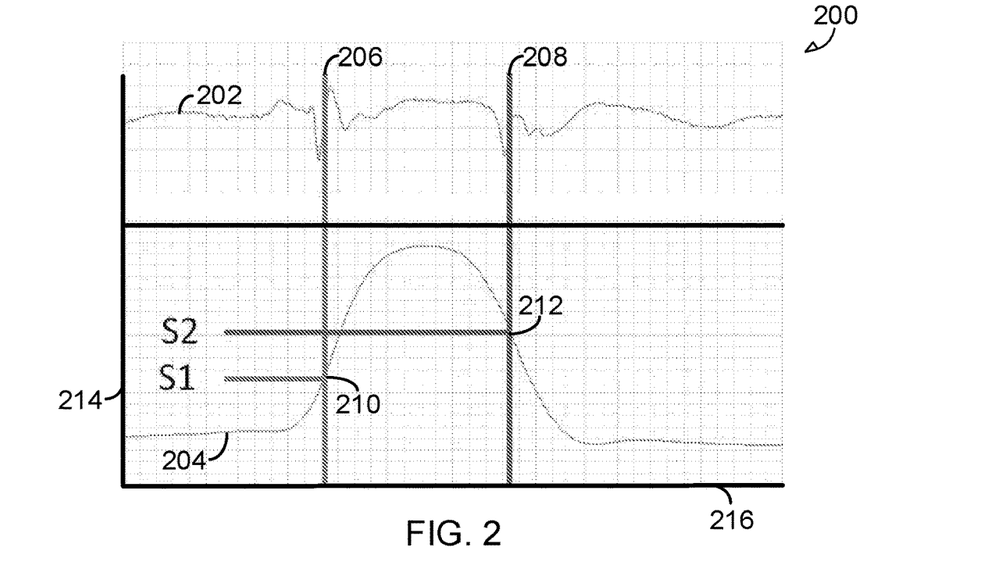
FIG. 2 illustrates generally an example relationship between a heart sound signal and a left ventricular pressure signal.

FIG. 2 illustrates generally an example relationship 200 between a heart sound signal 202 and a left ventricular pressure signal 204 with respect to amplitude 214 and time 216. The timing of the first and second heart sounds are illustrated at 206, 208, respectively, as well as the intersection of the S1 and S2 timings 206, 208 with the left ventricular pressure signal 204 at 210, 212, respectively.

The systemic systolic pressure can be conceptualized in FIG. 2 as the peak of the left ventricular pressure signal 204.

In contrast, the estimated systemic diastolic pressure can be conceptualized as the crossing of the S2 timing 208 with the left ventricular pressure signal 204 at 212, or as the crossing of the S1 timing 206 with the left ventricular pressure signal 204 at 210. In certain examples, to estimate the systemic diastolic pressure, at least one of the S1 or S2 timings 206, 208 can be adjusted by a respective correction factor, such as a time or amplitude correction along the left ventricular pressure signal 204.

Although illustrated with respect to a systemic diastolic pressure and a left ventricular pressure signal, the systems and methods disclosed herein can be used to estimate a pulmonary diastolic pressure using a right ventricular pressure signal, similar to as shown herein with respect to the left ventricular pressure signal 204.

Figure 3:
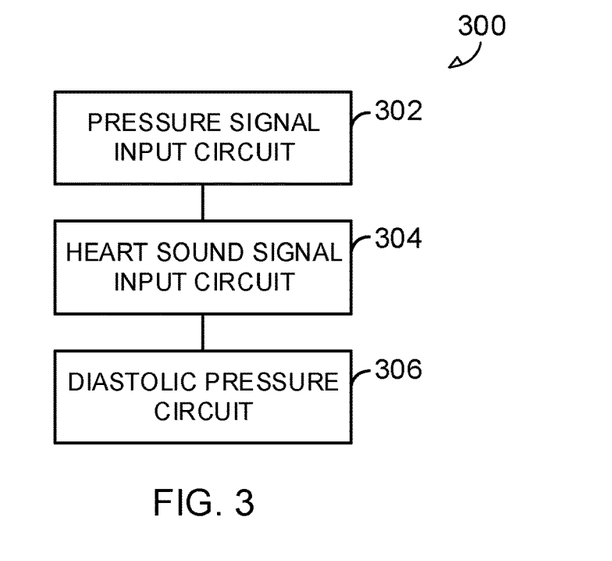
FIG. 3 illustrates generally an example system including a pressure signal input circuit, a heart sound signal input circuit, and an arterial diastolic pressure circuit.

FIG. 3 illustrates generally an example system 300 including a pressure signal input circuit 302, a heart sound signal input circuit 304, and an arterial diastolic pressure circuit 306. The pressure signal input circuit 302 can be configured to receive ventricular pressure information (e.g., left ventricular pressure information or right ventricular pressure information) of a heart of a patient. In an example, the ventricular pressure information of the heart of the patient can include a ventricular pressure signal (e.g., a left ventricular pressure signal or a right ventricular pressure signal). In other examples, the pressure signal input circuit can be configured to receive a table of values, or one or more other representation of the ventricular pressure of the heart.

The heart sound signal input circuit 304 can be configured to receive heart sound information of the heart of the patient. In an example, the heart sound information can include a heart sound signal, or the heart sound information can include one or more timings of one or more features of the heart sound signal, such as a timing of a first heart sound (S1), a timing of the second heart sound (S2), etc. The arterial diastolic pressure circuit 306 can be configured to estimate an arterial diastolic pressure of the patient using the ventricular pressure information of the heart and the heart sound information.

For example, the arterial diastolic pressure circuit 306 can be configured to estimate a systemic diastolic pressure of the patient using left ventricular pressure information of the heart over a first time interval and a timing of at least one of the S1 or the S2 in the first time interval, or a pulmonary diastolic pressure of the patient using right ventricular pressure information of the heart over a first time interval and a timing the at least one of the S1 or the S2 in the first timer interval. In certain examples, one or more of the timings of the S1 or the S2 can be adjusted by a respective correction factor, dependent on, for example, at least one of the ventricular pressure of the heart (e.g., left or right), a heart rate, an activity level, or a posture of the patient.

In an example, the system 300 can be implemented in a single device, such as an external programmer, or in multiple devices.

Figure 4:
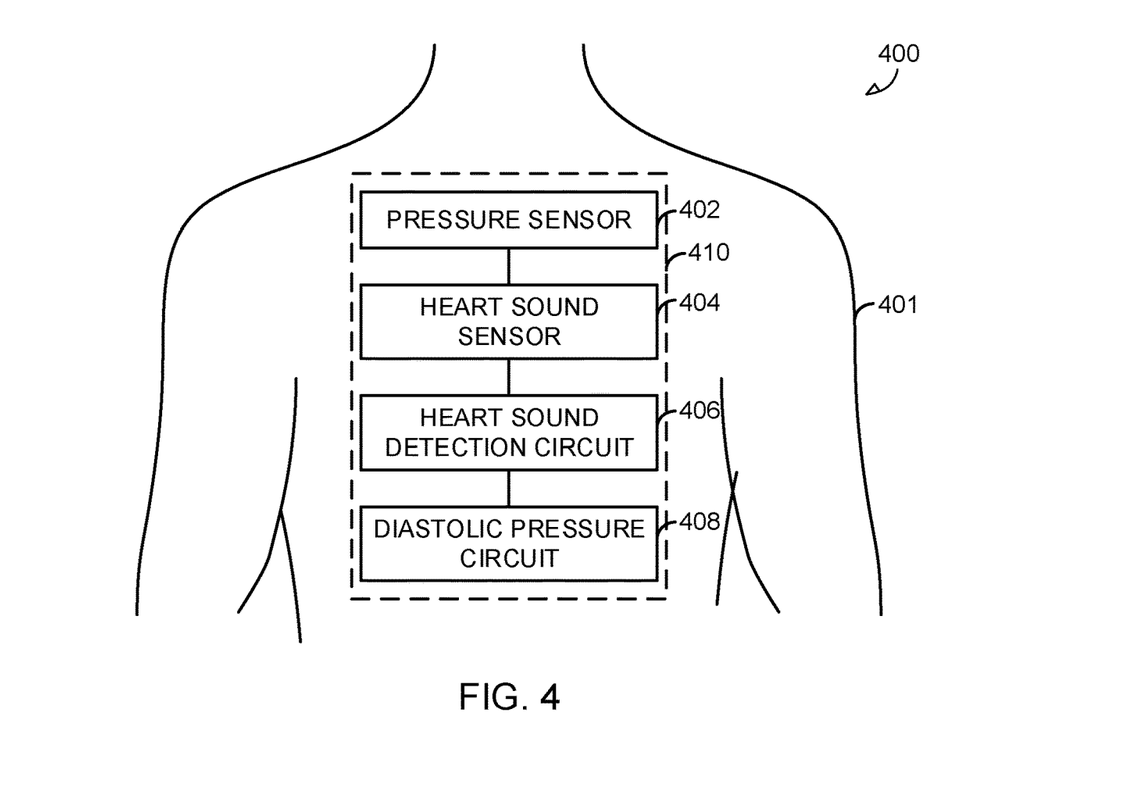
FIG. 4 illustrates generally an example system including an implantable medical device.

FIG. 4 illustrates generally an example system 400 including an implantable medical device 410, such as an implantable cardiac rhythm management (CRM) device, or one or more other implantable medical devices configured to detect a heart sound and a pressure signal of a patient 401.

In an example, the implantable medical device 410 can include each of a pressure sensor 402 configured to sense at least one of a left ventricular pressure or a right ventricular pressure of a heart of a patient 401 over a first time interval, a heart sound sensor 404 configured to sense a heart sound signal of the patient 401 over the first time interval, a heart sound detection circuit 406 configured to detect a timing of at least one of a first heart sound (S1) or a second heart sound (S2) in the first time interval using the heart sound signal, and an arterial diastolic pressure circuit 408 configured to estimate at least one of a systemic or a pulmonary diastolic pressure of the patient 401 using at least one of the left ventricular pressure or the right ventricular pressure over the first time interval and the timing of at least one of the S1 or the S2 in the first time interval, in certain examples, adjusted by one or more respective correction factors.

In other examples, one or more of the pressure sensor 402, the heart sound sensor 404, the heart sound detection circuit 406, or the systemic diastolic pressure circuit 408 can be components of separate implantable or external medical devices (e.g., a component of a leadless cardiac pacemaker (LCP), a medical device programmer, etc.).

The pressure sensor 402 and the heart sound sensor 404 can be in the same implantable medical device 401, or the pressure sensor 402 and the heart sound sensor 404 can be in separate devices. For example, the pressure sensor 402 can be included in an LCP device configured for placement in the left ventricle of the heart to sense a left ventricular pressure signal, whereas the heart sound sensor 404 can be a portion of a subcutaneous implantable medical device configured to wirelessly communicate with the pressure sensor 402. In other examples, both the heart sound sensor 404 and the pressure sensor 402 can be located on a single LCP, or on separate LCPs in a single patient.

The heart sound detection circuit 406 can be a component of the device having the heart sound sensor 404, or can be part of a separate implantable or external device, and can be configured to detect a timing of at least one of a first heart sound (S1) or a second heart sound (S2) in the first time interval using information from the heart sound sensor 404. Similarly, the arterial diastolic pressure circuit 408 can be a component of an implantable medical device or an external programmer configured to wirelessly communicate with the pressure sensor 402 and the heart sound sensor 404.

Figure 5:
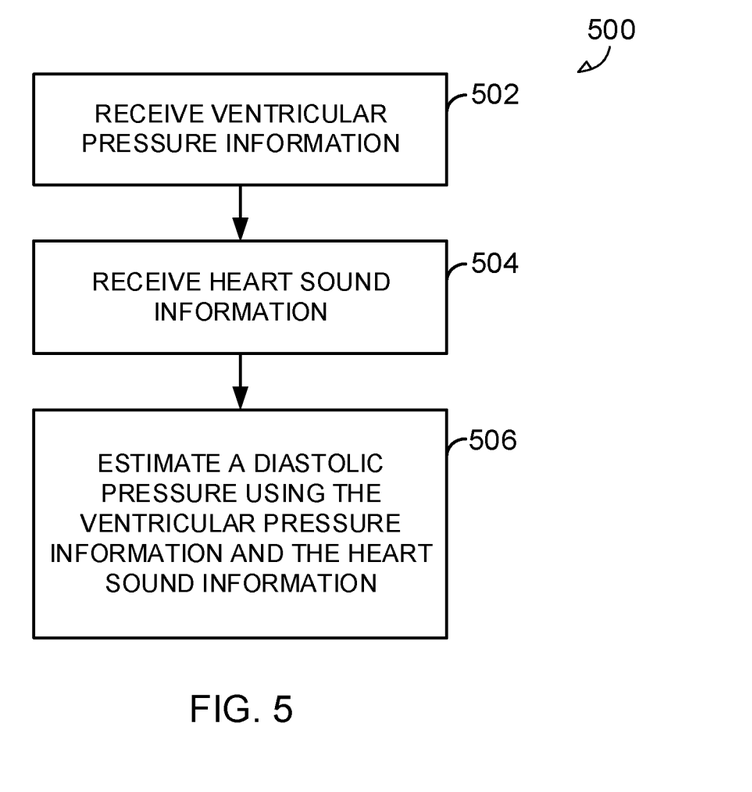
FIG. 5 illustrates generally an example method for estimating an arterial diastolic pressure of a patient.

FIG. 5 illustrates generally an example method 500 for estimating an arterial diastolic pressure of a patient (e.g., a systemic diastolic pressure or a pulmonary diastolic pressure). At 502, ventricular pressure information of a heart of a patient can be received (e.g., left ventricular pressure information or right ventricular pressure information), such as at a pressure signal input circuit, a pressure sensor, an external programmer, etc. At 504, heart sound information of the heart of the patient can be received, such as using a heart sound sensor, a heart sound signal input circuit, an external programmer, etc.

At 506, an arterial diastolic pressure of the patient (e.g., a systemic diastolic pressure or a pulmonary diastolic pressure, etc.) can be estimated using the ventricular pressure information of the heart (e.g., a left ventricular pressure signal, a right ventricular pressure signal, etc.) and the heart sound information of the heart (e.g., timings of the first heart sound (S1) or the second heart sound (S2).

Figure 6:
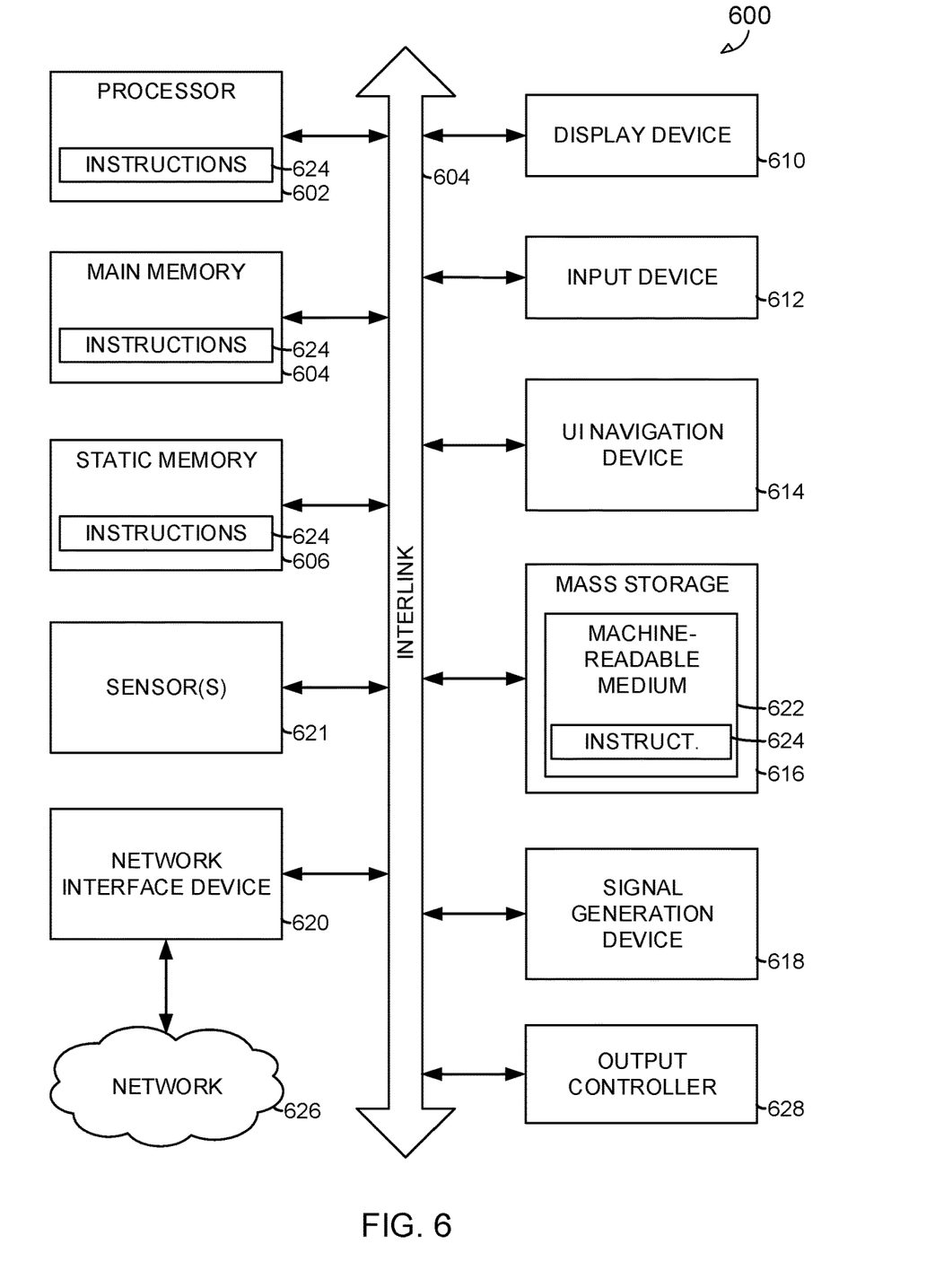
FIG. 6 illustrates generally a block diagram of an example machine upon which any one or more of the techniques (e.g., methodologies) discussed herein may perform.

FIG. 6 illustrates generally a block diagram of an example machine 600 upon which any one or more of the techniques (e.g., methodologies) discussed herein may perform. Portions of this description may apply to the computing framework of various portions of the LCP device, the IMD, or the external programmer.

In alternative embodiments, the machine 600 may operate as a standalone device or may be connected (e.g., networked) to other machines. In a networked deployment, the machine 600 may operate in the capacity of a server machine, a client machine, or both in server-client network environments. In an example, the machine 600 may act as a peer machine in peer-to-peer (P2P) (or other distributed) network environment. The machine 600 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Examples, as described herein, may include, or may operate by, logic or a number of components, or mechanisms. Circuit sets are a collection of circuits implemented in tangible entities that include hardware (e.g., simple circuits, gates, logic, etc.). Circuit set membership may be flexible over time and underlying hardware variability. Circuit sets include members that may, alone or in combination, perform specified operations when operating. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

Machine (e.g., computer system) 600 may include a hardware processor 602 (e.g., a central processing unit (CPU), a graphics processing unit (GPU), a hardware processor core, or any combination thereof), a main memory 604 and a static memory 606, some or all of which may communicate with each other via an interlink (e.g., bus) 608. The machine 600 may further include a display unit 610 (e.g., a raster display, vector display, holographic display, etc.), an alphanumeric input device 612 (e.g., a keyboard), and a user interface (UI) navigation device 614 (e.g., a mouse). In an example, the display unit 610, input device 612 and UI navigation device 614 may be a touch screen display. The machine 600 may additionally include a storage device (e.g., drive unit) 616, a signal generation device 618 (e.g., a speaker), a network interface device 620, and one or more sensors 621, such as a global positioning system (GPS) sensor, compass, accelerometer, or other sensor. The machine 600 may include an output controller 628, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

The storage device 616 may include a machine readable medium 622 on which is stored one or more sets of data structures or instructions 624 (e.g., software) embodying or utilized by any one or more of the techniques or functions described herein. The instructions 624 may also reside, completely or at least partially, within the main memory 604, within static memory 606, or within the hardware processor 602 during execution thereof by the machine 600. In an example, one or any combination of the hardware processor 602, the main memory 604, the static memory 606, or the storage device 616 may constitute machine readable media.

While the machine readable medium 622 is illustrated as a single medium, the term "machine readable medium" may include a single medium or multiple media (e.g., a centralized or distributed database, and/or associated caches and servers) configured to store the one or more instructions 624.

The term "machine readable medium" may include any medium that is capable of storing, encoding, or carrying instructions for execution by the machine 600 and that cause the machine 600 to perform any one or more of the techniques of the present disclosure, or that is capable of storing, encoding or carrying data structures used by or associated with such instructions. Non-limiting machine readable medium examples may include solid-state memories, and optical and magnetic media. In an example, a massed machine readable medium comprises a machine readable medium with a plurality of particles having invariant (e.g., rest) mass. Accordingly, massed machine-readable media are not transitory propagating signals. Specific examples of massed machine readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

The instructions 624 may further be transmitted or received over a communications network 626 using a transmission medium via the network interface device 620 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as WiFi®, IEEE 802.16 family of standards known as WiMax®), IEEE 802.15.4 family of standards, peer-to-peer (P2P) networks, among others. In an example, the network interface device 620 may include one or more physical jacks (e.g., Ethernet, coaxial, or phone jacks) or one or more antennas to connect to the communications network 626. In an example, the network interface device 620 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 600, and includes digital or analog communications signals or other intangible medium to facilitate communication of such software.

Additional Notes

An example (e.g., "Example 1") of subject matter (e.g., a system) may include a pressure signal input circuit configured to receive ventricular pressure information of a heart of a patient, a heart sound signal input circuit configured to receive heart sound information of the heart of the patient, and an arterial diastolic pressure circuit configured to estimate an arterial diastolic pressure of the patient using the ventricular pressure information and the heart sound information of the heart.

In Example 2, the subject matter of Example 1 may optionally be configured such that the ventricular pressure information of the heart of the patient includes a ventricular pressure signal of a ventricle of the heart over a first time interval, the heart sound information includes a timing of at least one of a first heart sound (S1) or a second heart sound (S2) in the first time interval, and the arterial diastolic pressure circuit is configured to estimate an arterial diastolic pressure of the patient using the ventricular pressure information and the timing of at least one of the S1 or the S2.

In Example 3, the subject matter of any one or more of Examples 1-2 may optionally be configured such that the heart sound information includes a timing of the S2 in the first time interval, and the arterial diastolic pressure circuit is configured to estimate an arterial diastolic pressure of the patient using a measurement of the ventricular pressure signal at the time of the S2, or at the time of the S2 adjusted by a correction factor.

In Example 4, the subject matter of any one or more of Examples 1-3 may optionally be configured such that the heart sound information includes a timing of the S1 in the first time interval, and the arterial diastolic pressure circuit is configured to estimate an arterial diastolic pressure of the patient using a measurement of the ventricular pressure signal at the time of the S1, or at the time of the S1 adjusted by a correction factor.

In Example 5, the subject matter of any one or more of Examples 1-4 may optionally be configured such that the correction factor is dependent on at least one of the left ventricular pressure of the heart, a heart rate, an activity level, or a posture of the patient.

In Example 6, the subject matter of any one or more of Examples 1-5 may optionally be configured such that the ventricular pressure signal includes a left ventricular pressure signal of a left ventricle of the heart over the first time interval, and the arterial diastolic pressure circuit is configured to estimate a systemic diastolic pressure of the patient using the left ventricular pressure signal and the timing of at least one of the S1 or the S2.

In Example 7, the subject matter of any one or more of Examples 1-6 may optionally be configured such that the ventricular pressure signal includes a right ventricular pressure signal of a right ventricle of the heart over the first time interval, and the arterial diastolic pressure circuit is configured to estimate a pulmonary diastolic pressure of the patient using the right ventricular pressure signal and the timing of at least one of the S1 or the S2.

In Example 8, the subject matter of any one or more of Examples 1-7 may optionally be configured such that the arterial diastolic pressure circuit is configured to estimate an arterial diastolic pressure of the patient using the ventricular pressure information, the timing of the S1, and the timing of the S2.

In Example 9, the subject matter of any one or more of Examples 1-8 may optionally include a leadless cardiac pacemaker (LCP), including a pressure sensor configured to receive physiologic information from a ventricle of the heart of the patient, and an implantable medical device (IMD), wirelessly coupled to the LCP, including a heart sound sensor configured to receive a heart sound signal from the heart of the patient.

An example (e.g., "Example 10") of subject matter (e.g., a method) may include receiving ventricular pressure information of a heart of a patient using a pressure signal input circuit, receiving heart sound information of the heart of the patient using a heart sound signal input circuit, and estimating, using an arterial diastolic pressure circuit, an arterial diastolic pressure of the patient using the ventricular pressure information and the heart sound information of the heart.

In Example 11, the subject matter of Examples 10 may optionally be configured such that receiving the ventricular pressure information of the heart of the patient includes receiving a ventricular pressure signal of a ventricle of the heart over a first time interval, receiving heart sound information includes receiving a timing of at least one of a first heart sound (S1) or a second heart sound (S2) in the first time interval, and estimating the arterial diastolic pressure of the patient includes using the ventricular pressure information and the timing of at least one of the S1 or the S2.

In Example 12, the subject matter of any one or more of Examples 10-11 may optionally be configured such that receiving the heart sound information includes receiving a timing of the S2 in the first time interval, and estimating the arterial diastolic pressure of the patient includes using a measurement of the ventricular pressure signal at the time of the S2, or at the time of the S2 adjusted by a correction factor.

In Example 13, the subject matter of any one or more of Examples 10-12 may optionally be configured such that receiving the heart sound information includes receiving a timing of the S1 in the first time interval, and estimating the arterial diastolic pressure of the patient includes using a measurement of the ventricular pressure signal at the time of the S1, or at the time of the S1 adjusted by a correction factor.

In Example 14, the subject matter of any one or more of Examples 10-13 may optionally be configured such that receiving the ventricular pressure signal includes receiving a left ventricular pressure signal of a left ventricle of the heart over the first time interval, and estimating the arterial diastolic pressure of the patient includes estimating a systemic diastolic pressure of the patient using the left ventricular pressure signal and the timing of at least one of the S1 or the S2.

In Example 15, the subject matter of any one or more of Examples 10-14 may optionally be configured such that receiving the ventricular pressure signal includes receiving a right ventricular pressure signal of a right ventricle of the heart over the first time interval, and estimating the arterial diastolic pressure of the patient includes estimating a pulmonary diastolic pressure of the patient using the right ventricular pressure signal and the timing of at least one of the S1 or the S2.

An example (e.g., "Example 16") of subject matter (e.g., a system) may include a pressure signal input circuit configured to receive ventricular pressure information of a heart of a patient, a heart sound signal input circuit configured to receive heart sound information of the heart of the patient, and an arterial diastolic pressure circuit configured to estimate an arterial diastolic pressure of the patient using the ventricular pressure information and the heart sound information of the heart.

In Example 17, the subject matter of Examples 16 may optionally be configured such that the heart sound information includes a timing of at least one of a first heart sound (S1) or a second heart sound (S2), and the arterial diastolic pressure circuit is configured to estimate an arterial diastolic pressure of the patient using the ventricular pressure information and the timing of at least one of the S1 or the S2.

In Example 18, the subject matter of any one or more of Examples 16-17 may optionally be configured such that the ventricular pressure information of the heart of the patient includes a ventricular pressure signal of a ventricle of the heart over a first time interval, the heart sound information includes a timing of the S2 in the first time interval, and the arterial diastolic pressure circuit is configured to estimate an arterial diastolic pressure of the patient using a measurement of the ventricular pressure signal at the time of the S2.

In Example 19, the subject matter of any one or more of Examples 16-18 may optionally be configured such that the ventricular pressure information of the heart of the patient includes a ventricular pressure signal of a ventricle of the heart over a first time interval, the heart sound information includes a timing of the S2 in the first time interval, and the arterial diastolic pressure circuit is configured to estimate an arterial diastolic pressure of the patient using a measurement of the ventricular pressure signal at the time of the S2 adjusted by a correction factor.

In Example 20, the subject matter of any one or more of Examples 16-19 may optionally be configured such that the ventricular pressure information of the heart of the patient includes a ventricular pressure signal of a ventricle of the heart over a first time interval, the heart sound information includes a timing of the S1 in the first time interval, and the arterial diastolic pressure circuit is configured to estimate an arterial diastolic pressure of the patient using a measurement of the ventricular pressure signal at the time of the S1 adjusted by a correction factor.

In Example 21, the subject matter of any one or more of Examples 16-20 may optionally be configured such that the correction factor is dependent on at least one of the ventricular pressure of the heart, a heart rate, an activity level, or a posture of the patient.

In Example 22, the subject matter of any one or more of Examples 16-21 may optionally be configured such that the pressure signal input circuit is configured to receive left ventricular pressure information of a left ventricle of the heart of the patient, and the arterial diastolic pressure circuit is configured to estimate a systemic diastolic pressure of the patient using the left ventricular pressure information and the timing of at least one of the S1 or the S2.

In Example 23, the subject matter of any one or more of Examples 16-22 may optionally be configured such that the pressure signal input circuit is configured to receive right ventricular pressure information of a right ventricle of the heart of the patient, and the arterial diastolic pressure circuit is configured to estimate a pulmonary diastolic pressure of the patient using the right ventricular pressure information and the timing of at least one of the S1 or the S2.

In Example 24, the subject matter of any one or more of Examples 16-23 may optionally be configured such that the arterial diastolic pressure circuit is configured to estimate an arterial diastolic pressure of the patient using the ventricular pressure information, the timing of the S1, and the timing of the S2.

In Example 25, the subject matter of any one or more of Examples 16-24 may optionally be configured such that a leadless cardiac pacemaker (LCP), including a pressure sensor configured to receive physiologic information from a ventricle of the heart of the patient, and an implantable medical device (IMD), wirelessly coupled to the LCP, including a heart sound sensor configured to receive a heart sound signal from the heart of the patient.

In Example 26, the subject matter of any one or more of Examples 16-25 may optionally include a therapy adjustment circuit configured to adjust a therapy using the estimated diastolic pressure.

An example (e.g., "Example 27") of subject matter (e.g., a method) may include receiving ventricular pressure information of a heart of a patient using a pressure signal input circuit, receiving heart sound information of the heart of the patient using a heart sound signal input circuit, and estimating, using an arterial diastolic pressure circuit, an arterial diastolic pressure of the patient using the ventricular pressure information and the heart sound information of the heart.

In Example 28, the subject matter of Example 27 may optionally be configured such that receiving heart sound information includes receiving a timing of at least one of a first heart sound (S1) or a second heart sound (S2), and estimating the arterial diastolic pressure of the patient includes using the ventricular pressure information and the timing of at least one of the S1 or the S2.

In Example 29, the subject matter of any one or more of Examples 27-28 may optionally be configured such that receiving the ventricular pressure information of the heart of the patient includes receiving a ventricular pressure signal of a ventricle of the heart over a first time interval, receiving the heart sound information includes receiving a timing of the S2 in the first time interval, and estimating the arterial diastolic pressure of the patient includes using a measurement of the ventricular pressure signal at the time of the S2.

In Example 30, the subject matter of any one or more of Examples 27-29 may optionally be configured such that receiving the ventricular pressure information of the heart of the patient includes receiving a ventricular pressure signal of a ventricle of the heart over a first time interval, receiving the heart sound information includes receiving a timing of the S2 in the first time interval, and estimating the arterial diastolic pressure of the patient includes using a measurement of the ventricular pressure signal at the time of the S2 adjusted by a correction factor.

In Example 31, the subject matter of any one or more of Examples 27-30 may optionally be configured such that receiving the ventricular pressure information of the heart of the patient includes receiving a ventricular pressure signal of a ventricle of the heart over a first time interval, receiving the heart sound information includes receiving a timing of the S1 in the first time interval, and estimating the arterial diastolic pressure of the patient includes using a measurement of the ventricular pressure signal at the time of the S1 adjusted by a correction factor.

In Example 32, the subject matter of any one or more of Examples 27-31 may optionally be configured such that receiving the ventricular pressure information includes receiving left ventricular pressure information of a left ventricle of the heart of the patient, and estimating the arterial diastolic pressure of the patient includes estimating a systemic diastolic pressure of the patient using the left ventricular pressure information and the timing of at least one of the S1 or the S2.

In Example 33, the subject matter of any one or more of Examples 27-32 may optionally be configured such that receiving the ventricular pressure information includes receiving right ventricular pressure information of a right ventricle of the heart of the patient, and estimating the arterial diastolic pressure of the patient includes estimating a pulmonary diastolic pressure of the patient using the right ventricular pressure information and the timing of at least one of the S1 or the S2.

In Example 34, the subject matter of any one or more of Examples 27-33 may optionally be configured such that estimating the arterial diastolic pressure of the patient includes using the ventricular pressure information, the timing of the S1, and the timing of the S2.

An example (e.g., "Example 35") of subject matter (e.g., a system) may include a pressure sensor configured to sense a ventricular pressure of a patient over a first time interval, a heart sound sensor configured to sense a heart sound signal of the patient over the first time interval, a heart sound detection circuit configured to detect a timing of at least one of a first heart sound (S1) or a second heart sound (S2) in the first time interval using the heart sound signal, an arterial diastolic pressure circuit configured to estimate an arterial diastolic pressure of the patient using the ventricular pressure over the first time interval and the timing of at least one of the S1 or the S2 in the first time interval.

An example (e.g., "Example 36") of subject matter (e.g., a system or apparatus) may optionally combine any portion or combination of any portion of any one or more of Examples 1-35 to include "means for" performing any portion of any one or more of the functions or methods of Examples 1-35, or a "machine-readable medium" (e.g., massed, non-transitory, etc.) including instructions that, when performed by a machine, cause the machine to perform any portion of any one or more of the functions or methods of Examples 1-35.

The above detailed description includes references to the accompanying drawings, which form a part of the detailed description. The drawings show, by way of illustration, specific embodiments in which the disclosure can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, the code can be tangibly stored on one or more volatile or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A system, comprising:
 a pressure signal input circuit configured to receive ventricular pressure information of a heart of a patient;
 a heart sound signal input circuit configured to receive heart sound information of the heart of the patient, wherein the heart sound information includes a timing of a first heart sound (S1); and
 an arterial diastolic pressure circuit configured to determine an arterial diastolic pressure of the patient using the ventricular pressure information of the heart of the patient and the timing of the S1 of the patient,
 wherein, to determine the arterial diastolic pressure of the patient, the arterial diastolic pressure circuit is configured to:
  determine a correction factor representative of an electromechanical activation time (EMAT) of the heart of the patient using physiologic information of the patient, and
  measure the ventricular pressure information of the patient at the timing of the S1 of the patient adjusted by the determined correction factor.

2. The system of claim 1, wherein the ventricular pressure information of the heart of the patient includes a ventricular pressure signal of a ventricle of the heart over a first time interval.

3. The system of claim 1, wherein the pressure signal input circuit is configured to receive left ventricular pressure information of a left ventricle of the heart of the patient.

4. The system of claim 1, wherein the pressure signal input circuit is configured to receive right ventricular pressure information of a right ventricle of the heart of the patient.

5. The system of claim 1, including:
 a leadless cardiac pacemaker (LCP), including a pressure sensor configured to receive physiologic information from a ventricle of the heart of the patient; and
 an implantable medical device (IMD), wirelessly coupled to the LCP, including a heart sound sensor configured to receive a heart sound signal from the heart of the patient,
 wherein the pressure signal input circuit is configured to receive the ventricular pressure information from the pressure sensor of the LCP, and
 wherein the heart sound signal input circuit is configured to receive the heart sound information from the heart sound sensor of the IMD.

6. The system of claim 1, including a therapy adjustment circuit configured to adjust a therapy using the determined arterial diastolic pressure.

7. A method, comprising:
 receiving ventricular pressure information of a heart of a patient using a pressure signal input circuit;
 receiving heart sound information of the heart of the patient using a heart sound signal input circuit, wherein the heart sound information includes a timing of a first heart sound (S1); and
 determining, using an arterial diastolic pressure circuit, an arterial diastolic pressure of the patient using the ventricular pressure information of the heart of the patient and the timing of the S1 of the patient,
 wherein determining the arterial diastolic pressure comprises:
  determining a correction factor representative of an electromechanical activation time (EMAT) of the heart of the patient using physiologic information of the patient, and
 wherein determining the arterial diastolic pressure of the patient comprises measuring the ventricular pressure information of the patient at the timing of the S1 of the patient adjusted by the determined correction factor.

8. The method of claim 7, wherein receiving the ventricular pressure information of the heart of the patient includes receiving a ventricular pressure signal of a ventricle of the heart over a first time interval.

9. The method of claim 7, wherein receiving the ventricular pressure information includes receiving left ventricular pressure information of a left ventricle of the heart of the patient.

10. The method of claim 7, wherein receiving the ventricular pressure information includes receiving right ventricular pressure information of a right ventricle of the heart of the patient.

11. A system, comprising:
- a pressure sensor configured to sense a ventricular pressure of a patient over a first time interval;
- a heart sound sensor configured to sense a heart sound signal of the patient over the first time interval;
- a heart sound detection circuit configured to detect a timing of a first heart sound (S1) in the first time interval using the heart sound signal; and
- an arterial diastolic pressure circuit configured to determine an arterial diastolic pressure of the patient using the ventricular pressure of the patient over the first time interval and the timing of the S1 in the first time interval,
- wherein, to determine the arterial diastolic pressure of the patient, the arterial diastolic pressure circuit is configured to:
  - determine a correction factor representative of an electromechanical activation time (EMAT) of the heart of the patient using physiologic information of the patient, and
  - measure the ventricular pressure of the patient at the timing of the S1 of the patient adjusted by the determined correction factor.

* * * * *